United States Patent [19]

Chinlund

[11] Patent Number: 5,749,725
[45] Date of Patent: May 12, 1998

[54] MOUNTING PLATE ASSEMBLY FOR USE WITH A DENTAL ARTICULATOR

[76] Inventor: Donald B. Chinlund, 208 E. Lakeshore Dr., Cary, Ill. 60013

[21] Appl. No.: 741,723

[22] Filed: Oct. 31, 1996

[51] Int. Cl.⁶ .................................................. A61C 11/00
[52] U.S. Cl. .................................................. 433/60
[58] Field of Search ..................................... 433/60, 54

[56] References Cited

U.S. PATENT DOCUMENTS

| | | | |
|---|---|---|---|
| D. 279,816 | 7/1985 | Mitchell, Sr. | D24/10 |
| D. 299,057 | 12/1988 | Tucker | D24/10 |
| D. 306,206 | 2/1990 | Huffman | D24/10 |
| D. 313,469 | 1/1991 | Tucker | D24/10 |
| D. 322,127 | 12/1991 | Raskin | D24/182 |
| 4,030,197 | 6/1977 | Linck, II et al. | 433/60 |
| 4,103,424 | 8/1978 | Benjamin et al. | 433/58 |
| 4,164,074 | 8/1979 | Lawler et al. | 433/65 |
| 4,169,314 | 10/1979 | Mercer et al. | 433/60 |
| 4,214,367 | 7/1980 | Mack et al. | 433/60 |
| 4,352,662 | 10/1982 | Lee | 433/56 |
| 4,687,442 | 8/1987 | Wong | 433/60 |
| 4,865,544 | 9/1989 | Scruggs | 433/64 |
| 4,865,546 | 9/1989 | Naylor | 433/60 |
| 5,141,433 | 8/1992 | Peterson | 433/64 |
| 5,334,017 | 8/1994 | Lang et al. | 433/57 |
| 5,380,199 | 1/1995 | Koutavas | 433/60 |
| 5,431,564 | 7/1995 | Guichet | 433/56 |

FOREIGN PATENT DOCUMENTS 2922045  12/1980  Germany ................. 433/60

*Primary Examiner*—John J. Wilson
*Attorney, Agent, or Firm*—Meroni & Meroni

[57] ABSTRACT

A mounting plate assembly is provided for use with a dental articulator. The mounting plate assembly includes a mounting plate structure having a plurality of raised portions on a first side thereof. The mounting plate structure has a pin member extending perpendicular from a second side thereof. A base plate structure includes a portion having a slot adapted to receive and end portion of the pin member. The slot is positionable with respect to the pin member from an unlocked position to a locked position upon movement of the portion of the base plate structure to secure the base plate structure and mounting plate structure in fixed position with one another.

22 Claims, 8 Drawing Sheets

1

MOUNTING PLATE ASSEMBLY FOR USE WITH A DENTAL ARTICULATOR

BACKGROUND OF THE INVENTION

1. Field of the Invention

The present invention relates generally to dental articulators. More particularly, the invention pertains to a mounting plate assembly for use with a dental articulator having upper and lower frames.

2. Description of the Prior Art

Various prior art dental articulators are known in the art for use in assisting a dental lab technician and dentist in the development of dental prostheses, such as dentures, crowns and bridges. The dental articulator provides simulated movement of a patient's jaw to enable the dentist to obtain necessary diagnostic information for patient treatment.

In use, casts or models of a patient's dental structures are prepared and secured to mounting plates. These mounting plates are then connected to upper and lower frames of the dental articulator for producing the jaw movement simulations. Typically, the mounting plates are connected with threaded screw attachments which can be both time consuming and cumbersome. Further, over time a period of time, the threaded portions are subject to wear and stripping, which requires replacement of the screw attachments.

To overcome the above described problems with prior art mounting plates, several attempts using magnetics are known. Generally, a base mounting plate is secured to the dental articulator and contains a magnet for producing magnetic attachment with a mated mounting plate that holds the dental cast. For example, U.S. Pat. No. 5,431,564 issued to Guichet discloses such a magnetic mounting plate assembly.

While such assemblies provide for an alternative form of attachment, they also suffer several disadvantages. In order for the magnetic assemblies to securely attach the mounting plates to the dental articulators, the magnetic attraction is fairly strong. In some cases, this attraction can be excessive which may cause difficulties in removing the mounting plates. In other cases, this attraction is too weak which can allow movement of the casts against each other resulting in errors. More importantly, the use of magnetics in any degree produces a potential problem when used in close proximity with computerized or electronic equipment. Dental offices and dental labs that typically house the dental articulators often contain computer equipment, such as personal computers and computerized ovens. Since such computer equipment typically contains magnetic storage mediums, such as floppy and hard disk drives, the exposure of such equipment to magnetic forces is highly undesirable.

As will be described in greater detail hereinafter, the present invention differs from those previously proposed to provide an improved mounting plate assembly and employs a number of novel features that render it highly advantageous over the prior art.

SUMMARY OF THE INVENTION

Accordingly, it is an object of this invention to provide a mounting plate assembly that allows for quick and accurate attachment and removal of the mounted dental casts from a dental articulator.

Another object of this invention is to provide a mounting plate assembly that is self aligning and requires less plaster to attach molds to the dental articulator.

Still another object of this invention is to provide a mounting plate assembly that is inexpensive to manufacture and can be used with a wide variety of existing commercially available dental articulators.

To achieve the foregoing and other objectives, and in accordance with the purposes of the present invention a mounting plate assembly is provided for use with a dental articulator. The mounting plate assembly includes a mounting plate structure having a plurality of raised portions on a first side thereof. The mounting plate structure has a pin member extending perpendicular from a second side thereof. A base plate structure includes a portion having a slot adapted to receive and end portion of the pin member. The slot is positionable with respect to the pin member from an unlocked position to a locked position upon movement of the portion of the base plate structure to secure the base plate structure and mounting plate structure in fixed position with one another.

In accordance with an aspect of the invention, the base plate structure has a slide lock slot. A slide lock member is movably engaged within the slide lock slot with the slide lock member defining the portion having the slot. Slide lock member is movable between the locked and unlocked positions to secure the mounting plate and base plate structures together.

In accordance with another embodiment of the invention, a side portion of the base plate structure is pivotally connected to a side portion of the mounting plate structure for movement between the mounting plate structure and base plate structure in planes generally parallel to one another. The assembly in this embodiment has a spaced apart distance between the mounting plate structure and base plate structure to generally define a frame slot adapted for receiving a frame of the dental articulator with the pin member being extendible through a hole in the frame.

Other objects, features and advantages of the invention will become more readily apparent upon reference to the following description when taken in conjunction with the accompanying drawings, which drawings illustrate several embodiments of the invention.

DETAILED DESCRIPTION OF THE PREFERRED EMBODIMENT

Figure 1:
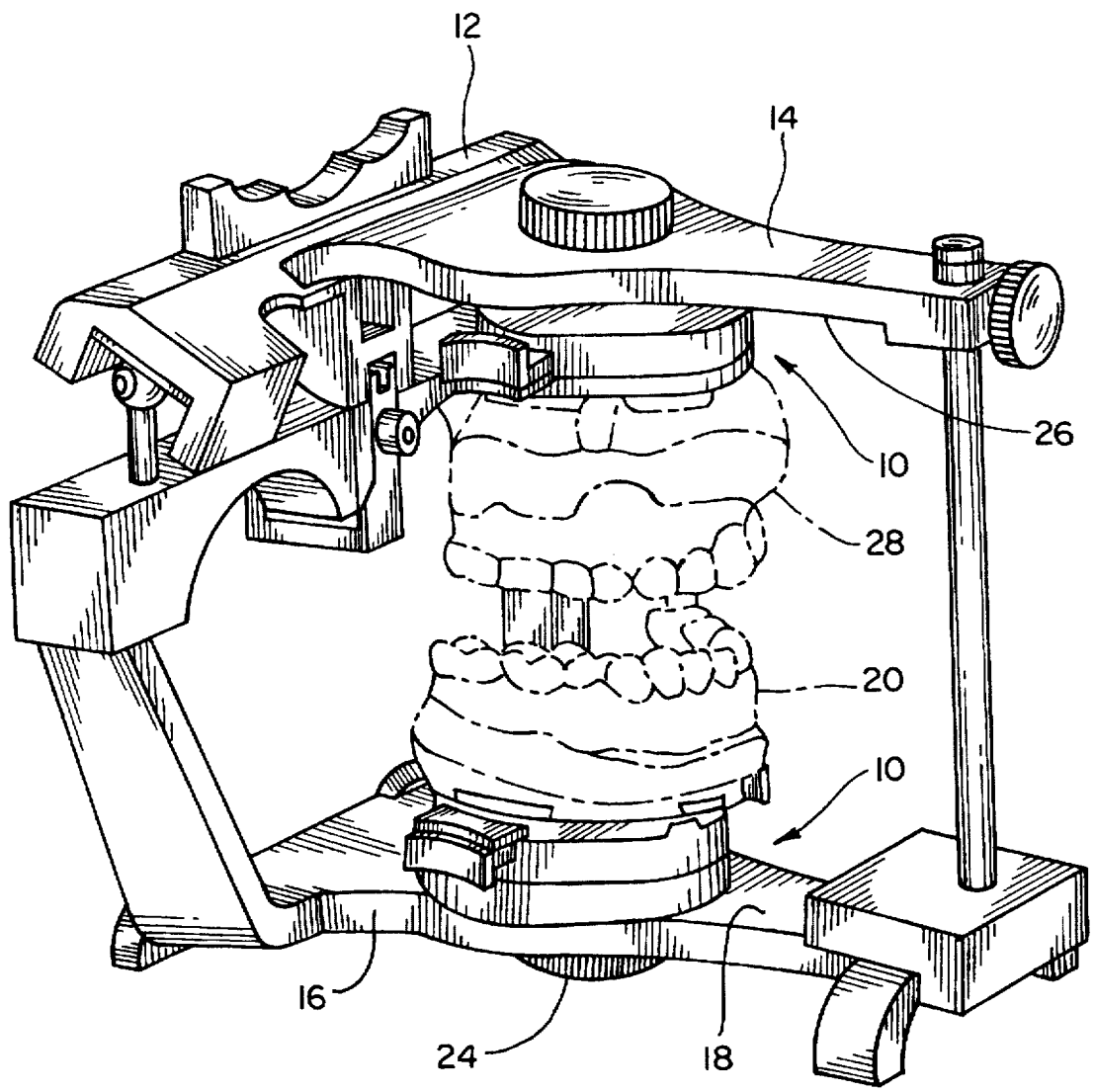
FIGS. 1–3 are perspective, partially exploded, and side views of a first embodiment of the present invention.
Figure 2:
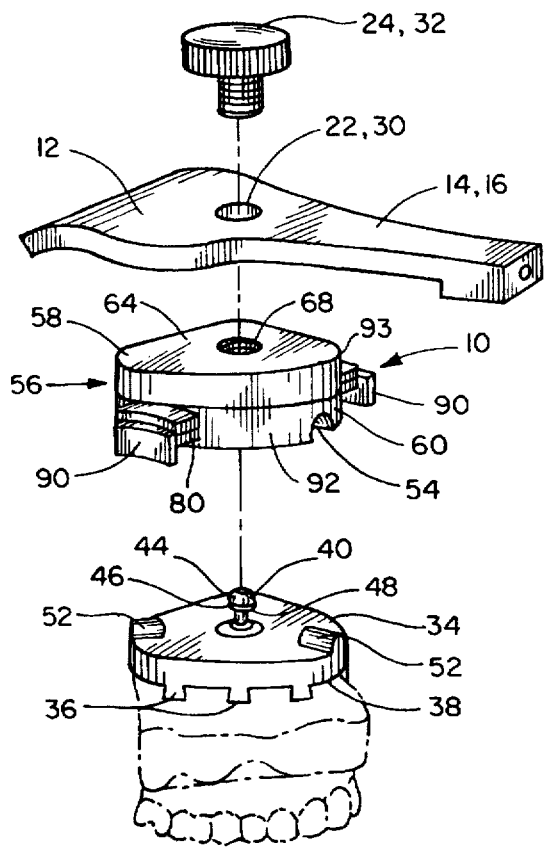
Figure 3:
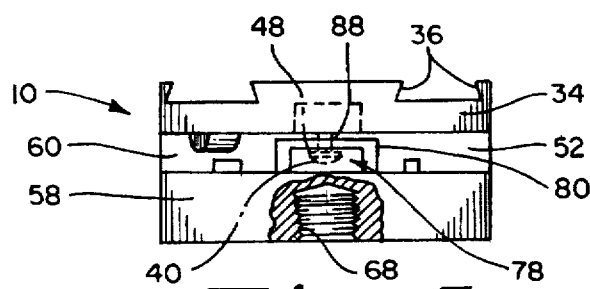
Figure 4:
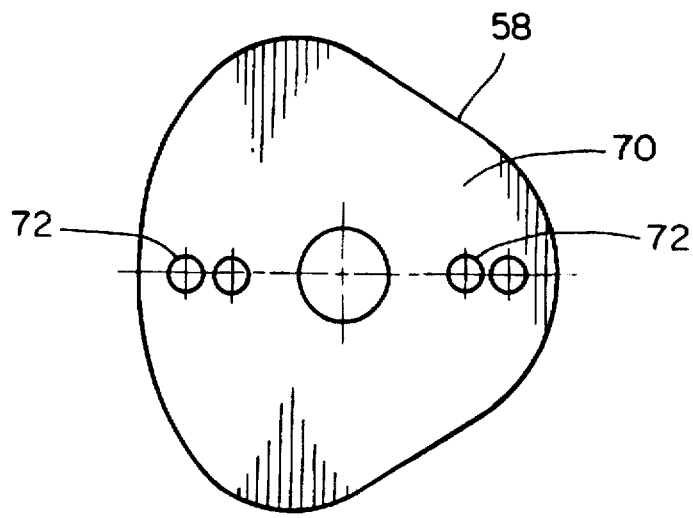
FIGS. 4–5 are top and bottom views of a first plate member of the base plate structure of the first embodiment.
Figure 5:
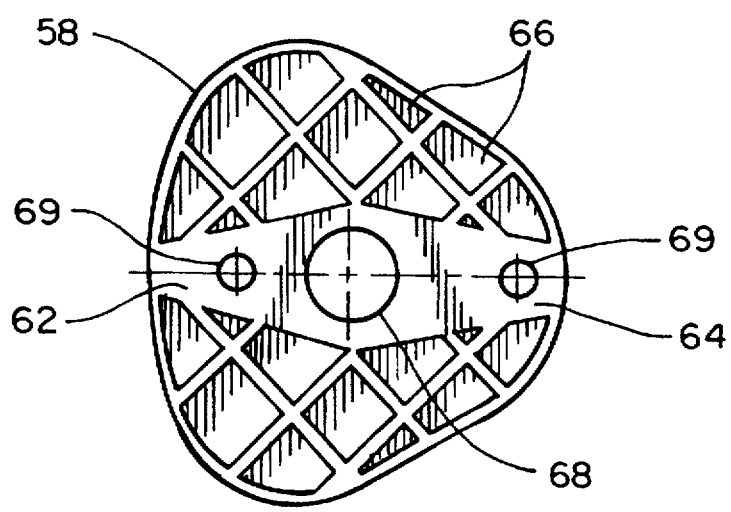
Figure 6:
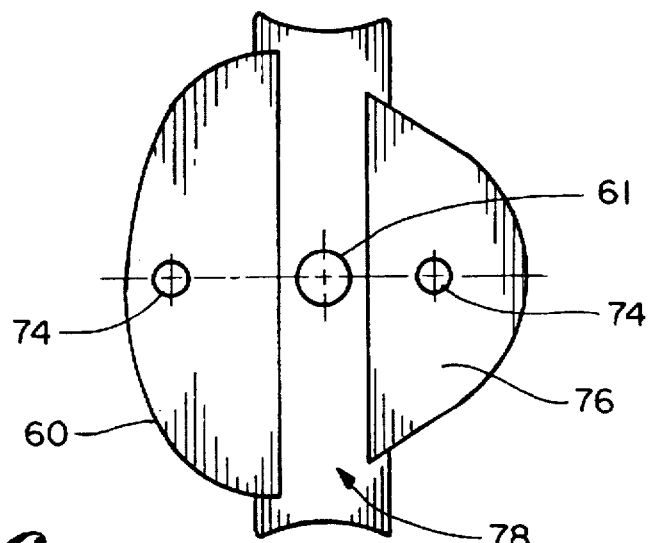
FIGS. 6–8 are top, side, and bottom views of a second plate member of the base plate structure of the first embodiment.
Figure 7:
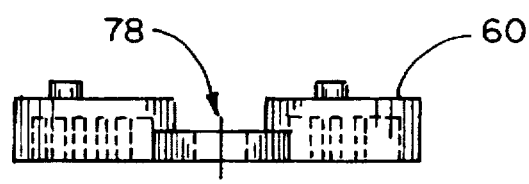
Figure 8:
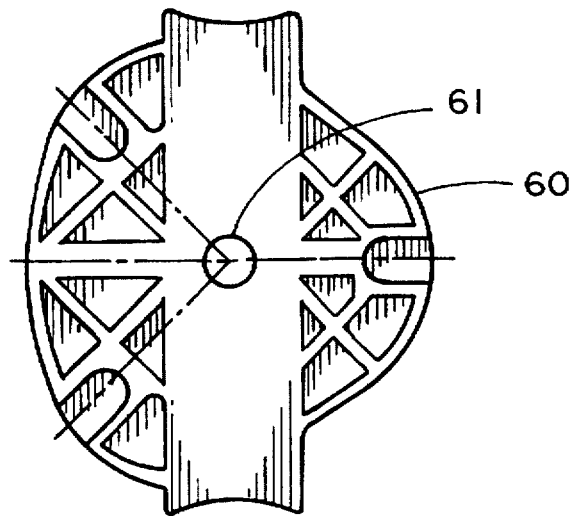
Figure 9:
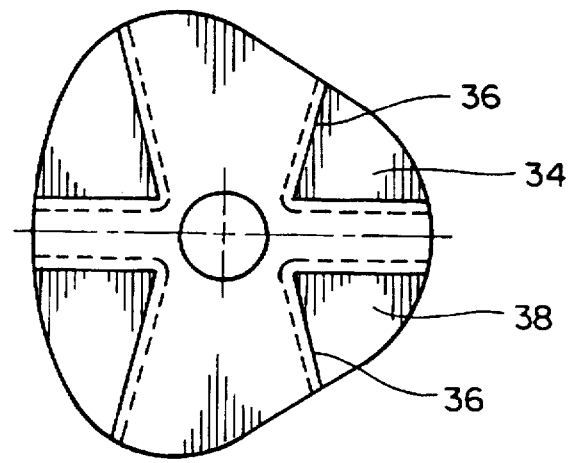
FIGS. 9–11 are top, side, and bottom views of a mounting plate structure of the first embodiment.
Figure 10:
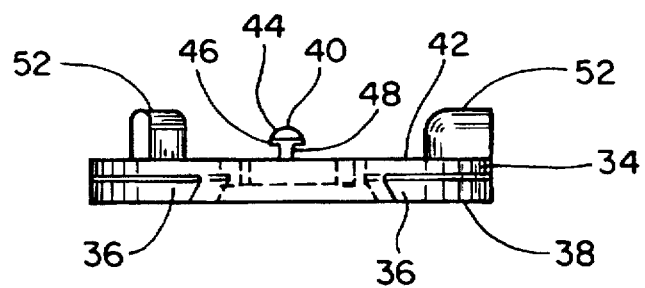
Figure 11:
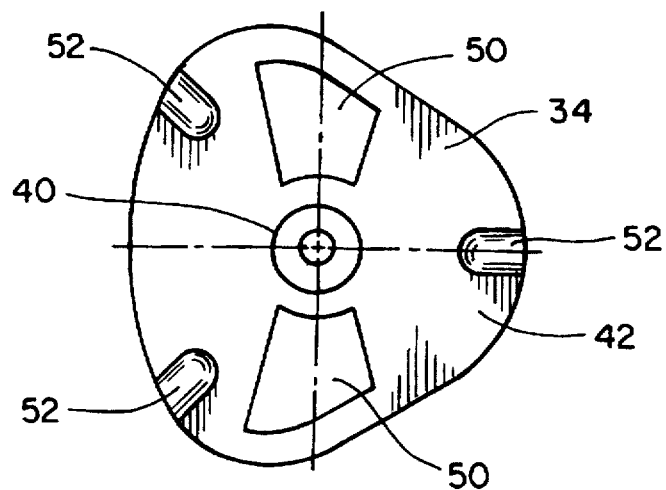

Referring now to the drawings, a first embodiment 10 of a mounting plate assembly for use with a dental articulator 12 is illustrated in FIGS. 1–3.

The dental articulator 12 is of the type having an upper frame 14 and a lower frame 16. The lower frame 16 has an upwardly facing area 18 for mounting an assembly 10 containing a dental cast 20 of the lower jaw of a patient. The lower frame 16 has a threaded hole 22 extending therethrough for threaded engagement with a threaded mounting screw 24. The upper frame 14 has a downwardly facing area 26 disposed above the lower frame 16 for mounting an assembly 10 containing a dental cast 28 of the upper jaw of a patient. The upper frame 14 has a threaded hole 30 extending therethrough for threaded engagement with a threaded mounting screw 32.

In general, different forms of articulators are distinguished with regard to their principle movement. It should be appreciated that the present invention is adapted for use with a wide variety of commercially known articulators in that many of these articulators are provided with the above described upper and lower frames 14, 16. Preferably, the articulator 12 is an arcon type articulator such as the Automark, Omni, and Combi dental articulators produced by Denar Corporation of 901 E. Cerritos Avenue, Anaheim, Calif.

Referring to FIGS. 2, and 9–11, a mounting plate structure 34 preferably formed of high-strength plastic is provided having a plurality of webs or raised portions 36 on a first side 38 of the mounting plate structure 34. The raised portions 36 are preferably dovetailed and provide surfaces for the plaster casts 20, 28 to adhere to during fabrication of the casts 20, 28. The mounting plate structure 34 has a metal pin member 40 extending perpendicular from a second side 42 of the mounting plate structure 34. An end portion 44 of the pin member 40 has an enlarged head 46. The head 46 has circular bottom edges 48. The second side 42 has recessed portions 50 to allow for less plastic being needed during manufacturing. Further, the second side 42 has outwardly extending alignment members 52 for aligned engagement in corresponding grooves 54 of a base plate structure 56 (FIG. 2).

Referring to FIGS. 2 and 4–8, the base plate structure 56 of the first embodiment of the assembly 10 is illustrated. Preferably, the base plate structure 56 is formed of high strength plastic and includes a first plate member 58 and second plate member 60 which are secured to one another. A top surface 62 of the first plate member 58 provides a first side 64 of the base plate structure 56 for engagement against the upper or lower frame 14, 16 of the articulator 12 (FIG. 1). The first side 64 has recessed portions 66 to allow for less plastic being needed during manufacturing. The first side 64 of the base plate structure 56 has a threaded hole 68 adapted for engagement with the mounting screw 24,32 of the dental articulator 12. A pair of small diameter holes 69 are provided on either sides of the threaded hole 68 to receive dowel pins of the articulator that will precisely orient the base plate structure 56 on the upper or lower frame 14, 16. A bottom surface 70 of the first plate member 58 has outwardly extending tabs 72 for snap fit engagement with receiving bores 74 on a top surface 76 of the second plate member 60. Adhesive may also be used to secure the first and second plate members 58, 60 together. The second plate member 60 of the base plate structure 56 has a slide lock slot 78 extending therein generally parallel with the sides and surfaces of the base plate structure 56. A pin receiving aperture 61 is provided in the second plate member 60 to allow the pin member 40 to have access within the slide lock slot 78. The slide lock slot 78 is sized and configured for receiving a slide lock member 80 (FIG. 3) for movably engagement therewithin.

Figure 12:
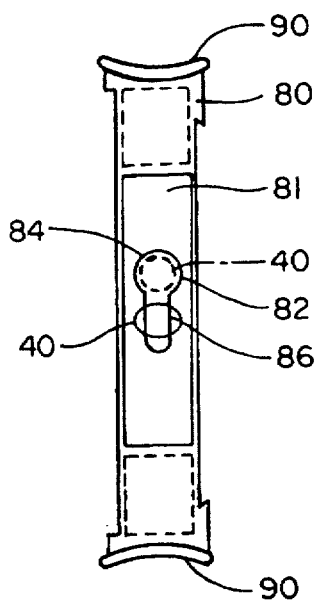
FIG. 12 is a top view of slide lock member of the base plate structure of the first embodiment.

Referring to FIGS. 3 and 12, the slide lock member 80 defines the portion 81 of the base plate structure 56 that has a slot 82 for engagement with the pin member 40 when the pin member 40 is inserted into the aperture 61. The slot 82 is preferably a bayonet type or keyhole shaped slot 82 having a rounded portion 84 have a diameter greater that the end portion 44 of the pin member 40 to allow the end portion 44 to extend through the rounded portion 84 when the slide lock member 80 is in an unlocked position. In the unlocked position, the aperture 61 and rounded portion 84 are in axial alignment with one another. The slot 82 has an inwardly tapered portion 86 having a diameter less than the end portion 44 or enlarged head 46 of the pin member 40 but greater than a shank portion 88 of the pin member 40 so that when the slide lock member 80 is moved from the unlocked to the locked position, the inwardly tapered portion 86 is in alignment with the aperture 61 and bottom edges 48 of the pin member 40 engage against the slide lock member 80 to produce a locking means for releasably engaging the pin member 40 to secure the base plate structure 56 and mounting plate structure 34 in fixed position with one another.

Figure 15:
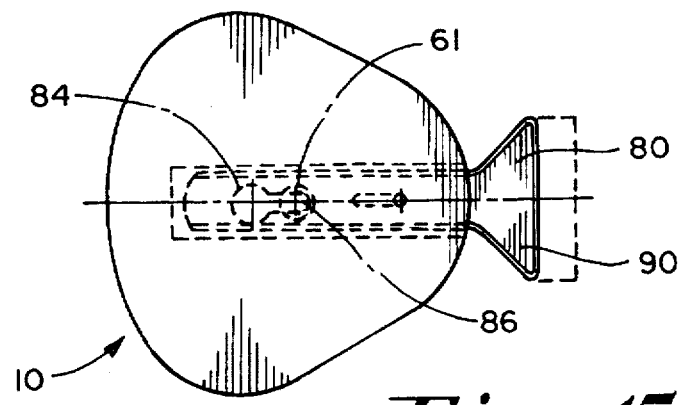
FIGS. 15–16 are top and side views of a third embodiment.
Figure 16:
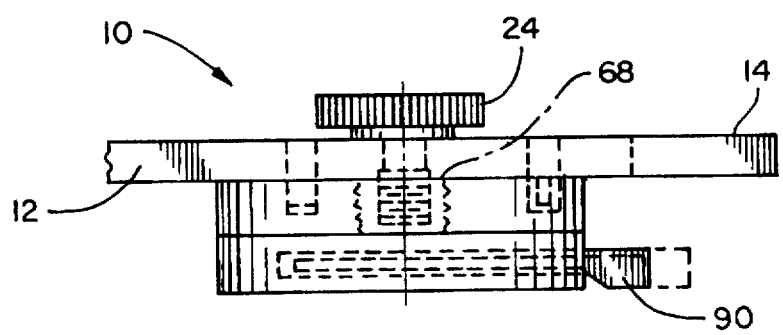
Figure 17:
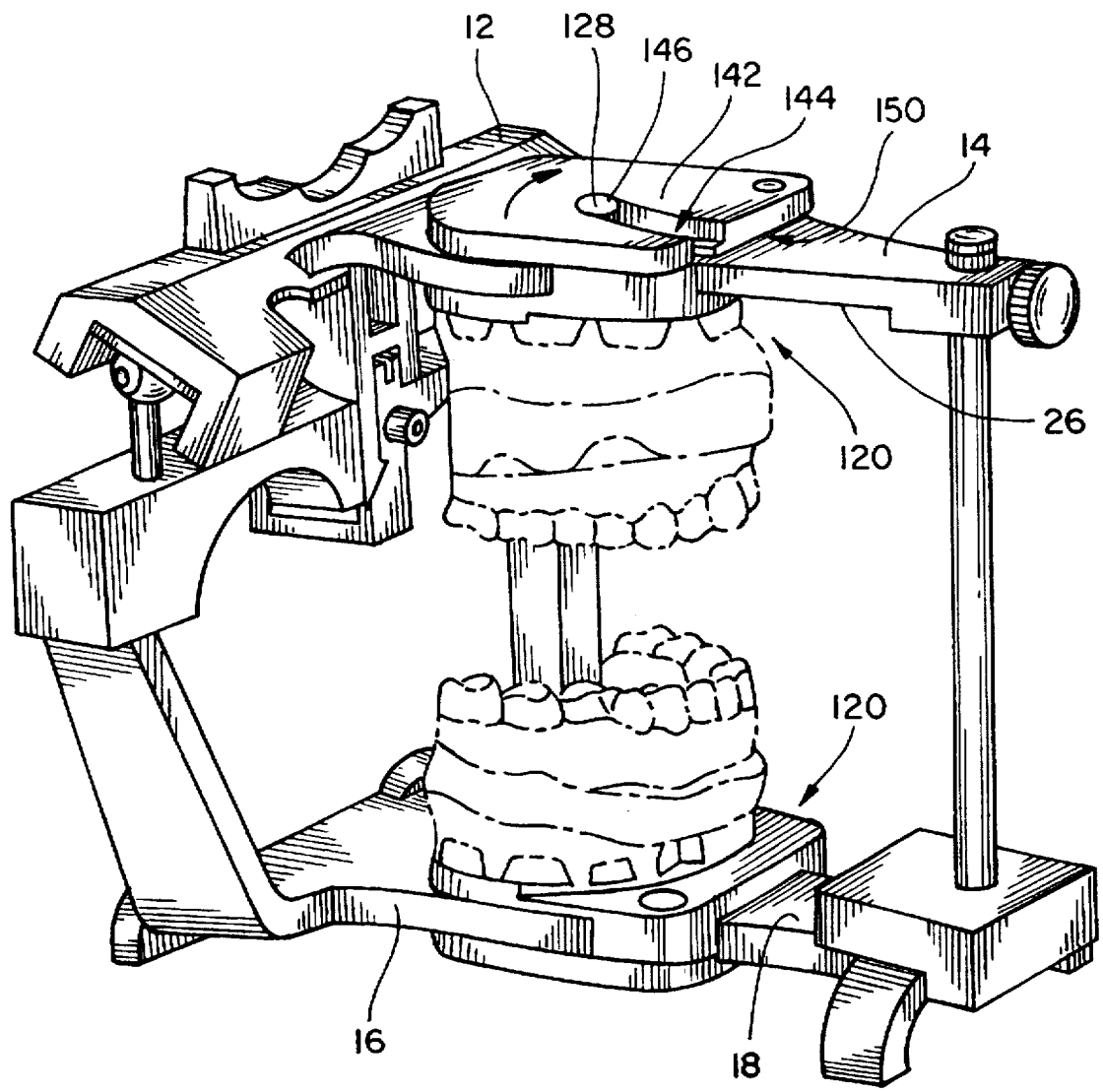
FIG. 17 is a perspective view of a fourth embodiment of the present invention.

The slide lock member 80 has an end member 90 extending outwardly from the slide lock slot 78 (FIG. 2). The end member 90 is sized and adapted for engagement by a user's finger. In the embodiment of FIG. 2, the slide lock member 80 has end members 90 extending on opposite sides 92, 93 of the base plate structure 56. In a third embodiment of assembly 10 shown in FIGS. 15 and 16, the slide lock member 80 has a single outwardly extending end member 90.

Figure 13:
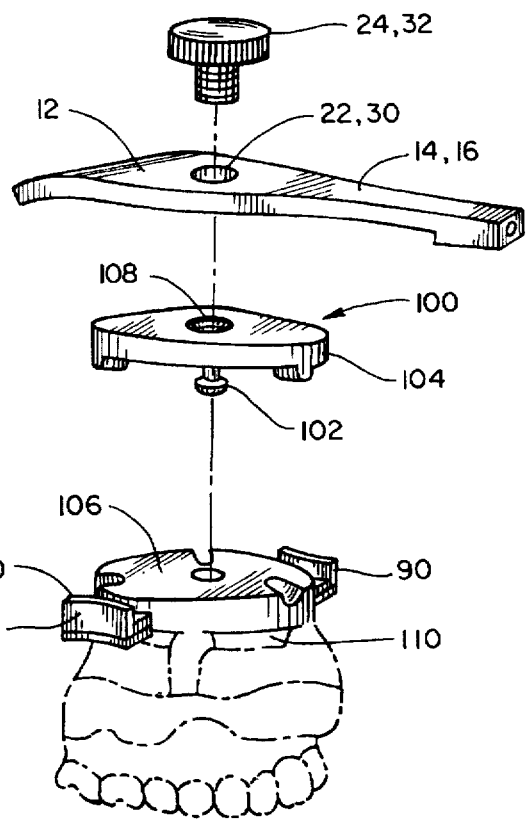
FIGS. 13–14 are partially exploded and side views of a second embodiment of the present invention.
Figure 14:
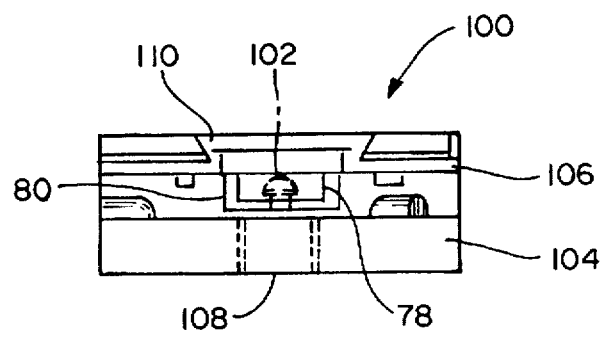

Referring to FIGS. 13 and 14, a second embodiment 100 of the the mounting plate assembly is illustrated. The features of embodiment 100 are similar to those as previously described in the first embodiment 10 except for the main differences that a pin member 102 is secured to and extends from a base plate structure 104 and the slide lock member 80 and related locking features are mounted to the mounting plate structure 106. In other words, embodiment 100 has essentially turned the embodiment of 10 around and has replaced the raised portions 36 of the mounting plate structure 34 of embodiment 10 with a threaded hole 108 for attachment with a threaded screw 24, 32 to produce base structure 104. In the base structure 56 of embodiment 10, the threaded hole 68 has been replaced with raised portions 110 to produce the mounting plate structure 106. Since the mounting plate structure 34, 106 is secured with each dental cast that is fabricated, reduced costs of manufacturing the mounting plate structure 34, 106 is desirous as this component will be sold in greater numbers than the corresponding base plate structure 56, 104. The assembly of embodiment 10 is therefore preferred over embodiment 100 in that the mounting plate structure 34 is less expensive to manufacture than the mounting plate structure 106 due to the simplified features. Further, embodiment 10 has a reduced height which aids in the storage of numerous structures 34 having dental casts secured thereto.

Referring to FIGS. 17–23, a fourth embodiment 120 of the mounting plate assembly is illustrated. A mounting plate structure 122 has a plurality of raised portions 124 on a first side 126 thereof. The mounting plate structure 122 has a pin member 128 extending perpendicular from a second side 130 of the mounting plate structure 122. The second side 130 has a plurality of recessed portions 132 in a web like configuration to reduce the amount of plastic material needed without compromising its strength.

A pair of small diameter holes 134 are provided on either sides of the pin member 128 to receive dowel pins of the articulator that will precisely orient the assembly 120 on the upper or lower frame 14, 16. A pivot member 136 is secured to respective corners or side portions 138, 139 of the mounting plate structure 122 and a base plate structure 140 to produce pivotal connection therebetween for movement between the mounting plate structure 122 and base plate structure 140 in planes generally parallel to one another.

Figure 18:
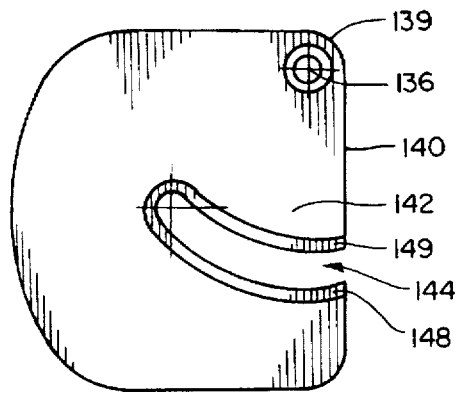
FIGS. 18–19 are top and bottom views of the base plate structure of the fourth embodiment.
Figure 19:
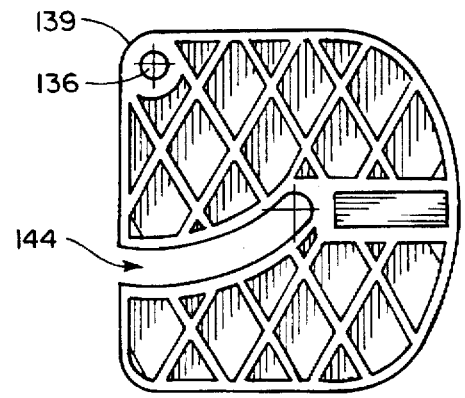
Figure 20:
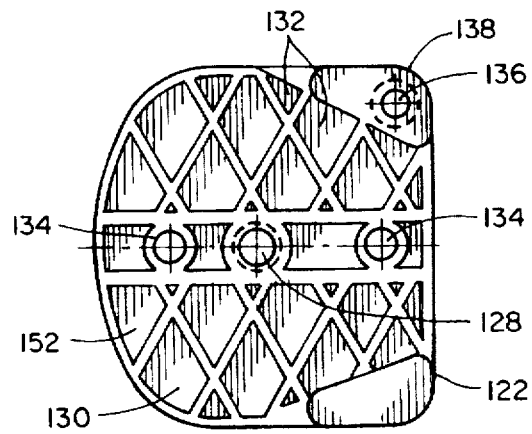
FIGS. 20–21 are top and bottom views of the mounting plate structure of the fourth embodiment.
Figure 21:
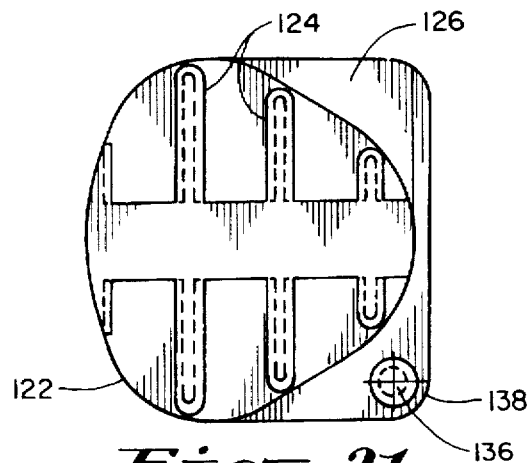
Figure 22:
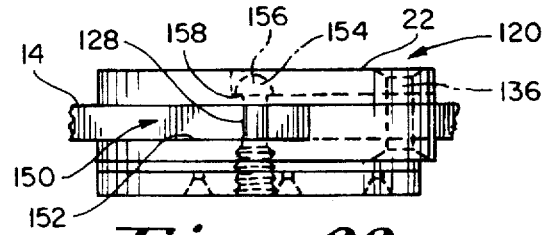
FIGS. 22–23 are side views of the fourth embodiment.
Figure 23:
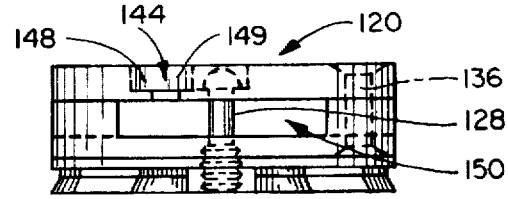

The base plate structure 140 has a portion 142 having a slot 144 adapted to receive an end portion 146 of the pin member 128. The slot 144 is positionable with respect to the pin member 128 by rotation or pivoting of the structures 122, 140 from an unlocked position remote from the pin member 128 for installation of the assembly 120 with the articulator 12 to a locked position to secure the structures 122, 140 in fixed position with one another with an upper or lower frame 14, 16 sandwiched therebetween. Preferably, the slot 144 is formed in a curved configuration, as best shown in FIGS. 18 and 19, such that each side edge 148, 149 of the slot 144 is approximately equal distance from the pivot member 136 along its length.

The mounting plate structure 122 and base plate structure 140 have a spaced apart distance therebetween to generally define a frame slot 150 (FIG. 22) adapted for receiving a frame 14,16 of the dental articulator 12. The pin member 128 is sized and adapted for extension through the hole 22, 30 in the frame 14, 16. Hence, assembly 120 does not require the mounting screws 24, 32 of the articulator 12.

In use, the base plate structure 140 is rotated about the pivot member 136 so that a frame receiving portion 152 the mounting plate structure 122 is not underlying the base plate structure 140. The frame receiving portion 152 is then placed in engagement against a corresponding frame 14, 16 with the pin member 128 extending through a respective hole 22, 30. The base plate structure 140 is then rotated such that an end portion 154 of the pin member 128 engages the slot 144. An enlarged head 156 of the pin member 128 has bottom edges 158 which engage with side edges 148, 149 of the slot 144.

Although the invention has been described by reference to some embodiments it is not intended that the novel device be limited thereby, but that modifications thereof are intended to be included as falling within the broad scope and spirit of the foregoing disclosure, the following claims and the appended drawings.

I claim:

1. In a dental articulator having a mounting plate assembly connected therewith, the mounting plate assembly being adapted for supporting a dental cast of a patient, the improvement of the mounting plate assembly comprising:
   (a) a mounting plate structure having a plurality of raised portions on a first side of the mounting plate structure, the mounting plate structure having a pin member extending perpendicular from a centermost portion of a second side of the mounting plate structure; and
   (b) a base plate structure including a portion having a slot adapted to receive an end portion of the pin member, the slot being positionable with respect to the pin member from an unlocked position to a locked position upon movement of the portion of the base plate structure to secure the base plate structure and mounting plate structure in fixed position with one another.

2. The mounting plate assembly of claim 1, wherein a side portion of the base plate structure is pivotally connected to a side portion of the mounting plate structure for movement between the mounting plate structure and base plate structure in planes generally parallel to one another.

3. The mounting plate assembly of claim 2, wherein the assembly includes a spaced apart distance between the mounting plate structure and base plate structure to generally define a frame slot adapted for receiving a frame of the dental articulator, the pin member being adapted for extension through a hole in the frame.

4. The mounting plate assembly of claim 1, wherein a first side of the base plate structure has a threaded hole adapted for engagement with a mounting screw of the dental articulator, the base plate structure having a slide lock slot extending therein generally parallel with the first side of the base plate structure, a slide lock member movably engaged within the slide lock slot, the slide lock member defining the portion having the slot with the slide lock member being movable between the locked and unlocked positions.

5. A mounting plate assembly for use with a dental articulator, the mounting plate assembly comprising:
   (a) a mounting plate structure having a plurality of raised portions on a first side of the mounting plate structure, the mounting plate structure having a pin member extending perpendicular from a centermost portion of a second side of the mounting plate structure; and
   (b) a base plate structure including a portion having a slot adapted to receive an end portion of the pin member, the slot being positionable with respect to the pin member from an unlocked position to a locked position upon movement of the portion of the base plate structure to secure the base plate structure and mounting plate structure in fixed position with one another.

6. The mounting plate assembly of claim 5, wherein a side portion of the base plate structure is pivotally connected to a side portion of the mounting plate structure for movement between the mounting plate structure and base plate structure in planes generally parallel to one another.

7. The mounting plate assembly of claim 6, wherein the assembly includes a spaced apart distance between the mounting plate structure and base plate structure to generally define a frame slot adapted for receiving a frame of the dental articulator, the pin member being adapted for extension through a hole in the frame.

8. The mounting plate assembly of claim 7, wherein the end portion of the pin member has an enlarged head, the head having a bottom edges in engagement with side edges of the slot.

9. The mounting plate assembly of claim 6, wherein the slot is formed in a curved configuration such that each side edge of the slot is approximately equal distance from a pivot member along its length, the pivot member being secured to the mounting plate structure and base plate structure.

10. The mounting plate assembly of claim 5, wherein a first side of the base plate structure has a threaded hole adapted for engagement with a mounting screw of the dental articulator, the base plate structure having a slide lock slot extending therein generally parallel with the first side of the base plate structure, a slide lock member movably engaged within the slide lock slot, the slide lock member defining the portion having the slot with the slide lock member being movable between the locked and unlocked positions.

11. The mounting plate assembly of claim 10, wherein the slide lock member has an end member extending outwardly from the slide lock slot, the end member being sized and adapted for engagement by a user's finger.

12. The mounting plate assembly of claim 10, wherein the slot is keyhole shaped.

13. In combination, a mounting plate assembly and dental articulator, comprising:
    (a) a dental articulator having upper and lower frames, each upper and lower frame having a threaded hole and a threaded mounting screw in threaded engagement therewith;
    (b) a mounting plate structure having a plurality of raised portions on a first side of the mounting plate structure, the mounting plate structure having a pin member extending perpendicular from a second side of the mounting plate structure; and
    (c) a base plate structure having locking means movably secured to the base plate structure for movement between an unlocked position and a locked position for releasably engaging the pin member to secure the base plate structure and mounting plate structure in fixed position with one another, a first side of the base plate structure having a threaded hole for removable engagement with the threaded mounting screw, the base plate structure having a slide lock slot extending therein generally parallel with the first side of the base plate structure, the locking means including a slide lock member movably engaged within the slide lock slot for lateral movement therewithin between the unlocked and locked positions, the slide lock member having a slot for releasable engagement with the pin member.

14. The combination of claim 13, wherein the slide lock member has an end member extending outwardly from the slide lock slot, the end member being sized adapted for engagement by a user's finger.

15. A mounting plate assembly for use with a dental articulator, the mounting plate assembly comprising:
    (a) a mounting plate structure having a plurality of raised portions on a first side of the mounting plate structure, the mounting plate structure having a pin member extending perpendicular from a second side of the mounting plate structure; and
    (b) a base plate structure pivotally connected to the mounting plate structure, the base plate structure having a slot adapted to receive an end portion of the pin member, the slot being positionable with respect to the pin member from an unlocked position to a locked position upon movement of the base plate structure to secure the base plate structure and mounting plate structure in fixed position with one another, the mounting plate structure and base plate structure having a spaced apart distance therebetween to generally define a frame slot adapted for receiving a frame of the dental articulator, the pin member being adapted for extension through a hole in the frame.

16. The mounting plate assembly of claim 15, wherein the end portion of the pin member has an enlarged head, the head having a bottom edges in engagement with side edges of the slot.

17. The mounting plate assembly of claim 16, wherein the slot is formed in a curved configuration such that each side edge of the slot is approximately equal distance from a pivot member along its length, the pivot member being secured to the mounting plate structure and base plate structure.

18. In combination, a mounting plate assembly and dental articulator comprising:
    (a) a dental articulator having upper and lower frames, each upper and lower frame having a hole extending therethrough;
    (b) a mounting plate structure having a plurality of raised portions on a first side of the mounting plate structure, the mounting plate structure having a pin member extending perpendicular from a second side of the mounting plate structure; and
    (c) a base plate structure pivotally connected to the mounting plate structure, the base plate structure having a slot adapted to receive and end portion of the pin member, the slot being positionable with respect to the pin member from an unlocked position to a locked position upon movement of the base plate structure to secure the base plate structure and mounting plate structure in fixed position with one another, the mounting plate structure and base plate structure having a spaced apart distance therebetween to generally define a frame slot adapted for receiving a respective frame of the dental articulator, the pin member being extendible through the hole in the frame.

19. The combination of claim 18, wherein the end portion of the pin member has an enlarged head, the head having bottom edges in engagement with side edges of the slot, the slot is formed in a curved configuration such that each side edge of the slot is approximately equal distance from a pivot member along its length, the pivot member being secured to the mounting plate structure and base plate structure.

20. A mounting plate assembly for use with a dental articulator, the mounting plate assembly comprising:
    (a) a mounting plate structure having a plurality of raised portions on a first side of the mounting plate structure, the mounting plate structure having a pin member extending perpendicular from a second side of the mounting plate structure; and
    (b) a base plate structure including a portion having a slot adapted to receive an end portion of the pin member, the slot being positionable with respect to the pin member from an unlocked position to a locked position upon movement of the portion of the base plate structure to secure the base plate structure and mounting plate structure in fixed position with one another, a side portion of the base plate structure being pivotally connected to a side portion of the mounting plate structure for movement between the mounting plate structure and base plate structure in planes generally parallel to one another.

21. The mounting plate assembly of claim 20, wherein the assembly includes a spaced apart distance between the mounting plate structure and base plate structure to generally define a frame slot adapted for receiving a frame of the dental articulator, the pin member being adapted for extension through a hole in the frame.

22. A mounting plate assembly for use with a dental articulator, the mounting plate assembly comprising: a pair of plate structures, one of said plate structures having a pin member extending perpendicular from a side thereof, the other plate structure having locking means movably secured therewith for movement between an unlocked position and a locked position for releasably engaging the pin member to secure the pair of plate structures in fixed position with one another, said other plate structure having a slide lock slot extending therein generally parallel with the first side of the base plate structure, said locking means including a slide lock member movably engaged within the slide lock slot for lateral movement therewithin, the slide lock member having a slot for releasable engagement with the pin member.

* * * * *